United States Patent [19]
Suh et al.

[11] Patent Number: 5,846,075
[45] Date of Patent: Dec. 8, 1998

[54] ONE PACKAGE, SHELF-STABLE PHOTO-CURABLE BAND CEMENT

[75] Inventors: Byoung I. Suh, Oak Brook; Paul A. Gange, Itasca, both of Ill.

[73] Assignee: Bisco, Inc., Itasca, Ill.

[21] Appl. No.: 807,234

[22] Filed: Feb. 28, 1997

[51] Int. Cl.[6] .............................. A61C 3/00; A61F 2/00; A61K 6/08
[52] U.S. Cl. .......................... 433/23; 523/115; 523/116; 523/117; 523/118
[58] Field of Search ............................. 433/23; 533/115, 533/116, 117, 118; 106/35

[56] References Cited

U.S. PATENT DOCUMENTS

| | | | |
|---|---|---|---|
| 3,709,866 | 1/1973 | Waller | 260/27 R |
| 4,126,737 | 11/1978 | Gruber et al. | 526/270 |
| 4,218,294 | 8/1980 | Brack | 204/159.13 |
| 4,437,836 | 3/1984 | Schmitz-Josten et al. | 433/199 |
| 4,439,380 | 3/1984 | Michl et al. | 264/16 |
| 4,479,782 | 10/1984 | Orlowski et al. | 433/220 |
| 4,503,169 | 3/1985 | Randklev | 523/117 |
| 4,514,527 | 4/1985 | Bowen | 523/115 |
| 4,525,232 | 6/1985 | Rooney et al. | 156/273.3 |
| 4,544,359 | 10/1985 | Waknine | 523/115 |
| 4,746,685 | 5/1988 | Masuhara et al. | 522/13 |
| 4,775,727 | 10/1988 | Taylor | 525/454 |
| 4,788,254 | 11/1988 | Kawakubo et al. | 525/100 |
| 4,801,528 | 1/1989 | Bennett | 433/220 |
| 4,936,775 | 6/1990 | Bennett | 433/220 |
| 4,978,391 | 12/1990 | Jones | 106/35 |
| 5,015,180 | 5/1991 | Randklev | 433/9 |
| 5,035,621 | 7/1991 | Gottschalk et al. | 433/226 |
| 5,037,638 | 8/1991 | Hamer et al. | 424/52 |
| 5,130,347 | 7/1992 | Mitra | 522/149 |
| 5,348,988 | 9/1994 | Suh et al. | 523/118 |

*Primary Examiner*—Nicholas D. Lucchesi
*Attorney, Agent, or Firm*—Marshall, O'Toole, Gerstein, Murray & Borun

[57] ABSTRACT

A one package, shelf-stable, light-curing orthodontic band cement is disclosed. That cement comprises about 35 to about 80 weight percent finely divided inorganic filler, about 15 to about 45 weight percent of one or more dimethacrylate esters, zero to about 30 weight percent of one or more diluent mono- or trimethacrylate esters, about 5 to about 25 weight percent of one or more dimethacrylate esters containing two carboxylic acid groups and a photo-curing system present in an amount sufficient to effect cure within about two minutes or less upon direct irradiation of the cement with light. The cement's weight ratio of the dimethacrylate ester portion plus diluent mono- or trimethacrylate ester portion to the two carboxylic acid-containing dimethacrylate ester portion is about 3:1 to about 1.5:1. All of the methacrylates present constitute about 20 to about 65 weight percent of the cement. A process for using the cement to affix an orthodontic band to a tooth is also disclosed.

14 Claims, No Drawings

ONE PACKAGE, SHELF-STABLE PHOTO-CURABLE BAND CEMENT

FIELD OF THE INVENTION

The present invention relates to cements for adhering dental bands to teeth, and more particularly to photo-curable band cements that are provided from a single composition that requires no mixing prior to use and cures when irradiated by light, and to the use of such cements.

BACKGROUND OF THE INVENTION

Orthodontic bands are metallic, typically stainless steel, jackets that fit around teeth and to which the wire of dental braces is affixed. Such bands have been affixed to the teeth by means of several different types of cements. The bands are also typically solid metal and opaque to transmission of visible light.

Usually, those cements have been prepared from two or more active portions of solid and liquid that harden through chemical reaction when mixed together. Difficulties in using these cements that require mixing include batch to batch differences in viscosity and hardening times with concomitant differences in strength of the polymerized cement. Also, there is usually some waste because of the necessity to mix two or more portions and the difficulties encountered in accurately metering enough of the required components without substantial wastage. Such admixing shortly before use to avoid premature curing also complicates the procedure by introducing and additional step for the dental professional as well as lengthening the time spent by the patient in the treatment process.

In addition, adhesion to both the tooth enamel and the stainless steel band is required of a band cement. This dual binding helps to eliminate wash-out of the cement from between the tooth and band, as well as helps to prevent food particles from being trapped between the band and tooth.

Exemplary of these multi-part band cements are those so-called ionomer cements that cure in water upon the admixture of a polymeric electrolyte such as a polyacrylate or polymethacrylate and a reactive powder such as a calcium aluminum fluorosilicate glass powder whose surface region is depleted of calcium relative to the calcium concentration in the particle cores. These two-part ionomer cements also frequently contain a chelating agent that lengthens the working time with the cement and usually also the setting time.

U.S. Pat. No. 5,130,347 discloses a two-part ionomer cement that utilizes a photo-cure to hasten the setting time. Here, an oligomeric material having pendent carboxyl groups and pendent polymerizable groups is admixed in water with a reactive powder such as an above-discussed fluorositicate glass powder shortly before application to the tooth. The admixture so formed is then applied as desired, partially cured by exposure to light, and then permitted to harden by chemical reaction.

Another two-part photo-curable cement is disclosed in U.S. Pat. No. 3,709,866. In that patent, one part contains an aromatic dimethacrylate monomer or adduct with a mono- or diisocyanate, a diluent monomer and polymerization inhibitor. The second part contains an ultraviolet light-sensitive material that can initiate free radical polymerization when irradiated by ultraviolet light.

The use of one-component dental adhesive systems with ingredients seemingly similar to U.S. Pat. No. 3,709,866 are disclosed in U.S. Pat. No. 4,801,528 and its division, U.S. Pat. No. 4,936,775. These patents disclose adhesive systems which rely on curing from visible light which is transmitted through the tooth or through a light-transmitting article being affixed to the tooth.

U.S. Pat. No. 4,978,391 discloses an intraoral medicament delivery system and cement. Here, an oligomeric prepolymer admixed with a medicament is applied to a tooth with or without an orthodontic bracket, which covers only a part of the tooth but does not surround the tooth. The prepolymer is selected so that upon irradiation with light a soft elastomeric polymer is formed that can be removed from the tooth using dental tools. The prepolymer-medicament mixture can also include diluent monomers. The system described is not used for cementing the bracket to the tooth, but rather as a medicament delivery means or to provide a cushioning effect.

U.S. Pat. No. 5,015,180 discloses a dental tape having a curable paste sandwiched between two cover sheets as well as an orthodontic bracket having a curable paste on one side that acts as an adhesive. The paste is said to be comprised of about 10–40 percent resin, 60–90 percent filler and 0.1 to about 5 percent, more preferably 0.1 to about 1.0 percent photoinitiator. For use in adhering an orthodontic bracket, the paste is preferably said to contain 10 to 70 percent resin and 30–90 percent filler. An exemplary paste was said to contain equal weights of 2,2-bis[4-(3-methacryloxy-2-hydroxypropoxy)-phenyl]propane [BISGMA] and tetraethyleneglycol dimethacrylate [4EGDMA] along with 0.25 weight percent camphorquinone and 0.5 weight percent dimethylaminophenethanol. That admixture was then further mixed with various fillers.

Another single package photo-curable cement for orthodontic brackets is disclosed in U.S. Pat. No. 4,479,782. This composition is said to contain a mixture of (1) an aromatic or hydroaromatic acrylate or methacrylate having at least two ethylenic double bonds, (2) an aliphatic acrylate or methacrylate, (3) an alpha, beta-diketone and a tertiary amine. The cement is cured by irradiation with light on the opposite side of the tooth from the bracket unless transparent or metal brackets with perforated bases are used.

Improved photopolymerizable dental cements are said to be disclosed in U.S. Pat. No. 4,437,836. The disclosed improvements of that patent relate to the use of a particular alkylaminoarylsulfonyl photoactivator. Exemplary photopolymerizable cements based on particle-filled 2:1 BISGMA:4EGDMA compositions are disclosed.

Improvements in the photoinitiating ketone-amine system of a dental cement are said to be disclosed in U.S. Pat. No. 4,439,380. Here use of β-substituted tertiary amines is disclosed to provide the advantage.

Another improvement to a filled photo-curable dental material is disclosed in U.S. Pat. No. 4,544,359. The mixture there is said to contain 20–30 weight percent methacrylic ester monomer, 65–79 weight percent inorganic filler and 1–5 percent colloidal fumed silica. The improvement here is said to reside in a wet milling of the filler at a pH value of 5–7, followed by a wet milling-surface etching step and a milling-silanizing step in a solution of silane.

A further improvement in a photo-curable dental adhesive system is disclosed in U.S. Pat. No. 4,746,685. There, a usual mixture of methacrylate esters such as BISGMA and 4EGDMA is cured by irradiation of an organic peroxide and a pyrilium salt as the initiator.

A still further improvement in photo-curable dental adhesives is described in U.S. Pat. No. 5,035,621. In that patent, the improvement is disclosed to lie in the use of an ionic dye-counter ion as a photoinitiator. Thus, a visible light-absorbing dye that is ionically bonded to a reactive counter ion is used so that upon excitation of the dye, the counter ion donates or accepts an electron to or from the excited dye. That electron transfer process generates radicals that initiate polymerization.

BRIEF SUMMARY OF THE INVENTION

The present invention contemplates a shelf-stable, one package photo-curable orthodontic band cement. That cement comprises about 35 to about 80, and more preferably about 60 to about 75, weight percent finely divided inorganic filler, about 15 to about 45, preferably about 15 to about 30, weight percent of one or more dimethacrylate esters, zero to about 30 weight percent of one or more diluent mono- or trimethacrylate esters, about 5 to about 25, preferably about 7 to about 15, weight percent of one or more dimethacrylate esters containing two carboxylic acid groups and a photo-curing system present in an amount sufficient to effect cure within about two minutes or less upon irradiation of the cement with light. The cement's weight ratio of the dimethacrylate ester portion plus diluent mono- or tri-methacrylate ester portion to the two carboxylic acid group-containing dimethacrylate ester portion is about 3:1 to about 1.5:1, and all of the methacrylates constitute about 20 to about 65, preferably about 25 to about 40, weight percent of the cement.

A process of cementing an orthodontic band to a tooth is also contemplated. In accordance with that process, an above-described cement is applied to the tooth to be bonded, the inside of the band or both and the band is positioned around the tooth. The applied cement on the banded tooth is then irradiated with sufficient quanta of sufficiently energetic light to cure the cement; i.e., a cement-curing amount of light, and affix the band to the tooth.

The present invention has several benefits and advantages.

Perhaps the most salient benefits of the invention are that a contemplated shelf-stable, photo-curable orthodontic cement is provided in one package so that no product mixing is required by the user and there is consequently little, if any, use-to-use variance in the product viscosity or other properties.

Another benefit of the invention is that the adhesion between the cured cement and orthodontic stainless steel band is the same as can be achieved with a previously available two-part photo-curable cement.

An advantage of a contemplated cement is that curing can be effected in a time of two minutes or less, preferably about 20–30 seconds of irradiation, while obtaining the desired adhesion to the dental band, and without the need for use of light transparent or perforated bands or strong light sources capable of irradiation through the surface of the tooth.

A still further advantage of a contemplated cement is that adhesion occurs not only between the cured cement and dental band, but also between the cured cement and tooth.

Still further benefits and advantages of the present invention will become apparent to a skilled worker from the disclosure that follows.

DETAILED DESCRIPTION OF THE INVENTION

The present invention contemplates a shelf-stable, light-curing (photo-curable) orthodontic band cement. That cement comprises about 35 to about 80 weight percent finely divided inorganic filler, about 15 to about 45 weight percent of one or more dimethacrylate esters, zero to about 30 weight percent of one or more diluent mono- or trimethacrylate esters, about 5 to about 25 weight percent of one or more dimethacrylate esters containing two carboxylic acid groups and a photo-curing system present in an amount sufficient to effect cure within about two minutes upon irradiation of said cement with light. The weight ratio of the dimethacrylate ester portion plus diluent mono- or trimethacrylate ester portion to the two carboxylic acid-containing dimethacrylate ester portion is about 3:1 to about 1.5:1, and all of the methacrylates constitute about 20 to about 65 weight percent of the cement.

Exemplary finely divided fillers are oxides of aluminum, zirconium and silicon, silicate glasses, barium or strontium glasses, silanized-glass as disclosed in U.S. Pat. No. 4,544,359, whose disclosures are incorporated by reference, calcium carbonate and the like as are well-known, and that are inert to the other ingredients and the environment of the mouth. The contemplated filler particles have an average size of about 5 to about 10 microns or less.

Excellent fillers are the pyrogenic silicas, whose BET surface area is between 30 and 400 $m^2g$. Fillers produced by precipitation are also useful. Although the average grain size of the primary particles in pyrogenically produced fillers does not exceed an upper limit of 70 nm; particle sizes up to 10 $\mu$m, are obtained.

Colloidal fumed silica is also useful and can constitute all or part of the filler. The fumed silica is of sub-micron particle size, generally exhibiting an average particle size of from about 0.01 to about 0.2 microns and more usually about 0.05 to about 0.10 microns. The use of colloidal fumed silica helps to provide hydrophobicity to the resulting composite and thereby minimizes water sorption in the finally cured cement. In addition, the fumed silica contributes to better marginal integrity or adaptability and less marginal leakage. Also, handling characteristics such as bulk and consistency are improved. Flow and/or slump are minimized for better restoration placement in cavity preparations.

The colloidal fumed silica, when used, is preferably admixed with the methacrylate ester monomer system (discussed hereinafter) until a homogeneous mixture is obtained. Thereupon, the remaining inorganic filler is admixed therewith to form a homogeneous liquid. Exemplary fumed silica is available under the trademark AEROSIL®R-972 or OX-50 from DeGussa, Corporation, Ridgefield, N.J. A $ZrO_2/SiO_2$ filler is prepared as discussed in Example 6 of U.S. Pat. No. 4,503,169.

Further useful fillers are described in the before-noted U.S. patents, whose disclosures are incorporated by reference. Such fillers may also include caries inhibiting agents such as slow releasing fluoride agents to help inhibit caries from forming in the adjacent tooth structure. For example, glass ionomer 1X 1944 from Ferro Corporation, Cleveland, Ohio, which contains such a slow release fluoride agent, has utility in the present invention.

The finely divided fillers are present at about 35 to about 80 weight percent of a contemplated orthodontic band cement, and are more preferably present at about 60 to about 75 weight percent of the cement.

Exemplary dimethacrylate esters useful in a contemplated light-curing band cement include neopetylglycol dimethacrylate, decanediol-1,10-dimethacrylate, dodecanediol-1,12-dimethacrylate, 1,4-butanediol dimethacrylate, ethyleneglycol dimethacrylate, diethyleneglycol dimethacrylate, triethyleneglycol dimethacrylate (3EGDMA), tetraethyleneglycol dimethacrylate (4EGDMA), polyethyleneglycol dimethacrylate, propyleneglycol dimethacrylate, dipropyleneglycol dimethacrylate, tripropyleneglycol dimethacrylate, tetrapropyleneglycol dimethacrylate, polypropyleneglycol dimethacrylate, hexamethyleneglycol dimethacrylate (HMDA), 2,2-bis(4-methacryloxyphenyl)propane, 2,2-bis(4-methacryloxyethoxyphenyl)propane, 2,2-bis[4-(3-methacryloxy-2-hydroxypropoxy)phenyl]-propane (BISGMA), 1,2-bis(3-methacryloxy-2-hydroxypropoxy) ethane, CPDM—the reaction product of cyclopentane tetracarboxylic acid dianhydride and 2 moles of hydroxyethyl methacrylate (HEMA), tetrahydrofurfuryl cyclohexene dimethacrylate (TCDM)—the reaction product of Epiclon B-4400 (Dainippon Inc. and Chemicals Inc., Ft. Lee, N.J.) with 2 moles of HEMA, 2,2-bis(4-methacryloxyphenyl) propane, 2-hydroxy-1,3-dimethacryloxypropane, di-2-methacryloxyethyl-2,2,4-trimethylhexamethylene dicarbamate (UDMA), di-2-methacryloxyethylisophorone dicarbamate, and di-2-methacryloxyethyl-2,4- or 2,6-tolylene dicarbamate. Of the above monomers, the use of BISGMA and/or UDMA, CPDM, TCDM and 3EGDMA are presently preferred. Those monomers are usually so used as a mixture of about equal weights of either BISGMA, CPDM, TCDM or UDMA with 3EGDMA.

Exemplary diluent mono- or trimethacrylate ester monomers include 2-hydroxyethyl methacrylate, methacryloyl-2-hydroxypropyl trimellitate, methacryloyl 2-hydroxyethyl trimellitate, 2-hydroxy-3-phenoxypropyl methacrylate, trimethylolpropane trimethacrylate and pentaerythritol trimethacrylate. In preferred practice, a diluent mono- or trimethacrylate ester monomer is absent; or present at zero weight percent.

Further useful methacrylate esters are disclosed in the before-discussed U.S. patents, whose disclosures are incorporated herein by reference.

The dimethacrylate ester or esters are present at about 15 to about 45 weight percent of a contemplated photocurable orthodontic band cement, and more preferably at about 15 to about 30 weight percent. The diluent mono- or trimethacrylate ester monomer or monomers are preferably absent, but when present can be used to replace up to about 30 weight percent of the dimethacrylate ester portion, so the diluent ingredient(s) can be present at zero to about 30 weight percent of the composition. However, even if about 30 weight percent of a diluent mono- or trimethacrylate ester or esters are present, at least about 15 weight percent of a dimethacrylate ester or esters are also present.

Exemplary useful dimethacrylate ester monomers that contain two carboxyl groups per molecule are disclosed in U.S. Pat. No. 4,514,527 and No. 5,348,988 for bonding to dentin in systems other than those disclosed here, such as a metal primer in the latter patent and as part of a multilayered system used to help bond polymeric composites to dentin enamel in the former patent.

These materials are most easily described as being a reaction product of two moles of 2-hydroxyethyl methacrylate (HEMA) or 2-hydroxypropyl methacrylate with one mole of an aromatic dianhydride. Exemplary aromatic dianhydrides include 3,3',4,4'-benzophenonetetracarboxylic dianhydride, pyromellitic dianhydride whose reaction product with HEMA is referred to as PMDA, 3,3',4,4'-biphenyltetracarboxylic dianhydride whose reaction product with HEMA is referred to as BPDM, bis-(3,4-phenyldicarboxylic anhydride)sulfone whose reaction product with HEMA is referred to as DSDM and bis-(3,4-phenyldicarboxylic anhydride)ether.

The dimethacrylate ester or esters containing two carboxyl groups is present at about 5 to about 25 weight percent of a contemplated orthodontic band cement, and more preferably at about 7 to about 15 weight percent.

The ratio of dimethacrylate ester portion plus diluent mono- or trimethacrylate ester portion to the two carboxylic acid-containing dimethacrylate ester portion is about 3:1 to about 1.5:1, and more preferably at about 2:1. Use of a lesser ratio of the dicarboxyl group-containing dimethacrylate monomer or monomers leads to lower strength of the cured cement, whereas use of more than the stated proportion leads to diminished product shelf life, presumably due to acid-catalyzed polymerization.

All of the methacrylate esters present, i.e., the dimethacrylate ester(s) plus diluent methacrylate(s), if used, plus the two carboxylic acid group-containing dimethacrylate ester(s), constitute about 20 to about 65 weight percent of a contemplated photo-curable band cement. More preferably, that amount is about 25 to about 40 weight percent.

Optionally, one or more of the resin components may include a caries inhibiting agent that helps to prevent or inhibit caries formation in the adjacent tooth structure. For example, the fluoride release monomer disclosed in U.S. Pat. No. 5,037,638, whose disclosure is incorporated by reference, may have utility in the present invention.

A photo-curing or photosensitive curing system is also included in a contemplated light-curable orthodontic band cement. A contemplated photo-curing system is activated to cure the cement by irradiation with visible or near UV light, e.g. light of a wavelength of about 380 to about 500 $\mu$m, is nontoxic and initiates rapid and efficient curing upon irradiation.

Such systems are well-known and typically include a photoinitiator that is usually benzophenone or a derivative, or an $\alpha$-diketone such as benzil or camphorquinone; camphorquinone being presently preferred. Also included is tertiary amine reductant. Exemplary tertiary amines include tributylamine, tripropylamine, N-alkyldialkanol amines such as N-methyldiethanolamine, N-propyldiethanolamine, N-ethyldiisopropanolamine and trialkandamines such as triethanolamine and triisopropanolamine. Further useful tertiary amines are specifically disclosed in U.S. Pat. No. 4,439,380 and No. 4,437,836, and are also more generally disclosed in the patents discussed before. Ethyl 4-dimethylamino benzoate (EDMAB) is a presently preferred tertiary amine reductant.

The photo-curing system is present in an amount sufficient to cure the cement to a desired strength within about two minutes upon irradiation with light as above. More preferably, the cure time is less than about one minute, and most preferably about 20 to about 30 seconds. In usual practice, both components of the photo-curing system constitute less than about two percent of the weight of the photo-curable band cement, and more preferably less than about 1 weight percent.

The above ingredients are present in approximate weight ratios of the total weight of the photo-curable orthodontic band cement, with the ratio of dimethacrylate ester portion containing two carboxyl groups per molecule to the other methacrylate-containing monomer(s) present being of greater importance than the other ratios for achieving the desired bond strength to the orthodontic band, while maintaining shelf life. Thus, the percentages of individual ingredients provided before are approximate and can in some instances add up to as much as 105 weight percent or about 97 weight percent. However, inasmuch as a skilled worker knows that a composition must contain 100 weight percent of its ingredients, adjustments in actual amounts used can be readily made.

Still further ingredients such as well-known UV absorbers such as Uvinul® 3000 available from BASF Corp. can be present at less than about 0.5 weight percent, as can polymerization inhibitors such as hydroquinone monomethyl ether (MEHQ) or 2,6-di-tert-butyl-4-methylphenol (BHT) that can be present at less than 0.1 weight percent, and more usually at less than 0.01 weight percent. MEHQ is preferred as the polymerization inhibitor.

No special priming treatment of either a tooth to be bonded or the orthodontic band is needed for use of a contemplated band cement. The band is usually sand blasted for cleaning prior to use, whereas the tooth is cleaned and can be acid-etched prior to cementing, but an etch step is not required.

In using a contemplated band cement, one simply applies a small amount to either or both of the tooth and band, and then the band is positioned around the tooth. Any excess cement noted can be removed by wiping at this step, prior to curing. Irradiation of the applied cement on the tooth between the tooth and the band in position around the tooth using sufficient quanta (flux) of light of an appropriate energy (about 380 to about 500 µm); i.e., a cement-curing amount of light, causes polymerization and cure of the cement within the previously discussed time frame. Although some irradiation may contact the cement from light passing through the tooth, it is believed that most of the utilized light contacts the cement as the light passes between the exterior surface of the tooth and the interior surface of the band, thereby avoiding the need for use of perforated bands or strong light source for irradiation through the tooth. Once the cement is cured, the orthodontic band can be used immediately as by attachment of a wire for the orthodontic device.

A cemented band can be removed by slitting the band and peeling the band away from the tooth. Thus, the adhesion between the tooth and cement is not stronger than the tooth itself.

Adhesion between the cured cement and unprimed, but clean and sand blasted stainless steel band is typically about 10 to about 20 megapascals (about 1450 to about 2900 pounds/inch$^2$) and is preferably about at least 10–12 megapascals (about 1450–1740 pounds/inch$^2$ psi). These strengths are measured using an INSTRON® universal testing instrument Model 11331 as described in U.S. Pat. No. 5,348,988 whose disclosures are incorporated by reference. These values are in good comparison to the value of 4–5 megapascals (580–725 psi) obtained for one two-part photo-curable composition commercial material [ORTHO™ L-C, Fuji G-C Dental Industrial Corporation, Tokyo, Japan] and 10–12 megapascals (1450–1740 psi) for another commercial two-part photo-curable cement [BANLOCK™; Bisco, Inc., Itasca, Ill.]

Useful devices for irradiation of the cement to effect cure are also well-known to skilled workers. Exemplary irradiation devices include a SPECTRA-LITE™ visible light source available from Pentron Corp., Wellingford, Conn.; a fiber optic halogen lamp (PLURAFLEX™ HL 150) made by Litema, Munich, Germany; "Optilux 400" light from Demetron, Danbury, Conn., and PRISMETICS® light available from L. D. Caulk Division of Dentsply International, Inc., Milford, Del. Again, further useful irradiation sources are disclosed in the before-discussed U.S. patents.

A contemplated light-curable orthodontic band cement has the viscosity of a paste or cake frosting in that little if any drip or slump occurs when the cement is applied to a vertical surface at human body temperature. This viscosity is achieved primarily by balancing the size and amount of fillers used.

A contemplated photo-curable band cement is substantially free of water or other non-reactive solvents, but need not be anhydrous. That is, water or a non-toxic solvent such as ethanol or glycerin may be present incidentally, but neither water nor solvent is added intentionally, and the band cement is preferably free of any solvent.

A contemplated orthodontic band cement is easily prepared. Thus, all of the organic materials are first admixed together; i.e., the methacrylate esters, photoinitiator system (amine and photosensitizer), UV absorber (if used) and inhibitor (if used) are first admixed to homogeneity. The filler is thereafter admixed, and the newly formed mixture is again admixed to homogeneity. The resulting photo-curable orthodontic band cement is then packaged in an opaque container such as a flexible plastic tube from which the cement can be squeezed or a syringe from which the cement can be extruded. Admixing is typically carried out in the absence of actinic light as is absorbed by the photosensitizer. Once prepared, such one component dental cement compositions are shelf-stable, exhibiting expected shelf lives of about 1–2 years when stored in their light-opaque containers at room temperature.

The following detailed description sets forth methods for preparation and use of the novel compositions of the present invention.

Example 1

An exemplary light-curable, shelf-stable orthodontic band cement was prepared using the following ingredients in the stated amounts:

| Ingredient | Weight % |
|---|---|
| Filler | |
| Glass Ionomer glass* (RWG) | 26.8 |
| Strontium silica* (RWG) | 36.18 |
| Ox-50* | 4.02 |
| Resins | |
| BISGMA[1] | 13.2 |
| 3EGDMA[2] | 9.25 |
| DSDM[3] | 9.9 |
| Photoinitiator System | |
| Photoinitiator (camphorquinone) | 0.15 |
| Amine (EDMAB) | 0.3 |
| U.V. Absorber | |
| (Uvinul ® 3000) | 0.2 |
| Inhibitor (MEHQ) | <0.01 |

*all from Ferro Corporation, Cleveland, Ohio and all treated with A-174 silane, Glass Ionomer glass is IX 1994 RWG and includes fluoride releasing agent
[1]2,2-Bis[4-(3-methacryloxy-2-hydroxypropoxy)phenyl]propane
[2]Triethyleneglycol dimethacrylate
[3]Reaction product of two moles of 2-hydroxyethyl methacrylate and one mole of bis-(3,4-phenyldicarboxylic anhydride)sulfone.

Adhesion between the cement and unprimed, but cleaned and sand blasted stainless steel band according to the above-described methods was about 10 MPa (about 1450 p.s.i.) after application of the cement and curing for about 20–30 seconds using the aforementioned Optilux 400 light source capable of delivering at least 400 milliwatts of continuous power, positioning the tip of such light source in close proximity to the occlusal surface of the tooth and band interface and moving the light source in a slow circle. The cement composition was fully cured within the above 20–30 second time frame.

Testing of the cement after packaging at elevated temperature of 37 degrees Centigrade reveals that it was stable for at least 3–6 months, which is believed to correspond to an expected shelf life of about 1–2 years if stored in its light-opaque container at room temperature.

Example 2

Another exemplary light-curable, shelf-stable orthodontic band cement was prepared using the ingredients from Example 1 and with the following variations and in the following stated amounts:

| Ingredient | Weight % |
| --- | --- |
| Filler | |
| Strontium silicate* (RWG) | 65.8 |
| Submicron silica* | |
| (same source as strontium silicate) | 4.2 |
| Resins | |
| BISGMA | 12.0 |
| 3EGDMA | 8.4 |
| TCDM | 9.0 |
| Photoinitiator System | |
| Photoinitiator (camphorquinone) | 0.1 |
| Amine (EDMAB) | 0.3 |
| U.V. Absorber | |
| (Uvinul ® 3000) | 0.2 |
| Inhibitor (MEHQ) | <0.01 |

When applied, light-cured and tested according to the methods of Example 1, this dental cement composition cured in the same time frame and exhibited shear bond strengths of about 12 MPa (about 1740 p.s.i.)

Example 3

Another exemplary light-curable, shelf-stable orthodontic band cement was prepared using the ingredients from Example 1 and with the following variations and in the following stated amounts:

| Ingredient | Weight % |
| --- | --- |
| Filler | |
| Strontium silicate* (RWG) | 65.8 |
| Submicron silica* | |
| (same source as strontium silicate) | 4.2 |
| Resins | |
| BISGMA | 9.0 |
| 3EGDMA | 8.4 |
| CPDM | 12.0 |
| Photoinitiator System | |
| Photoinitiator (camphorquinone) | 0.1 |
| Amine (EDMAB) | 0.3 |
| U.V. Absorber | |
| (Uvinul ® 3000) | 0.2 |
| Inhibitor (MEHQ) | <0.01 |

When applied, cured and tested according to the methods of Example 1, the cement of this Example cured in the same time frame and exhibited a shear bond strength of about 11 MPa (about 1595 p.s.i.)

The foregoing description and the examples are intended as illustrative and are not to be taken as limiting. Still other variations within the spirit and scope of this invention are possible and will readily present themselves to those skilled in the art. For example, a small amount of colorant may be added during formulation of the above cement compositions to assist the dental professional's viewing of the cement during its application to the band and subsequent seating of the band on the tooth. Colorants such as Macrolax Blue RR from Mobay Corp., Pittsburgh, Pa., in amounts of about 0.01 weight percent or less may be added in place of an equal amount of one of the resin components of the cement such as 3EDGMA.

We claim:

1. A one package, shelf-stable, light-curing orthodontic band cement that comprises about 35 to about 80 weight percent finely divided inorganic filler, about 15 to about 45 weight percent of one or more dimethacrylate esters, zero to about 30 weight percent of one or more diluent mono- or trimethacrylate esters, about 5 to about 25 weight percent of one or more dimethacrylate esters containing two carboxylic acid groups and a photo-curing system present in an amount sufficient to effect cure within about two minutes or less upon direct irradiation of said cement with light, wherein the weight ratio of the dimethacrylate ester portion plus diluent mono- or trimethacrylate ester portion to the two carboxylic acid-containing dimethacrylate ester portion is about 3:1 to about 1.5:1, and all of said methacrylates constitute about 20 to about 65 weight percent of said cement.

2. The light-curing orthodontic band cement according to claim 1 wherein said inorganic filler is present in an amount of about 60 to about 75 weight percent of the band cement.

3. The light-curing orthodontic band cement according to claim 1 wherein the non-carboxylic acid dimethacrylate ester portion is present at about 15 to about 30 weight percent of the band cement.

4. The light-curing orthodontic band cement according to claim 1 wherein the diluent mono- or trimethacrylate ester is absent.

5. The light-curing orthodontic band cement according to claim 1 wherein the carboxylic acid-containing methacrylate ester portion is present at about 7 to about 15 weight percent of the band cement.

6. The light curing orthodontic band cement according to claim 1 wherein one or more of said fillers or dimethacrylate esters includes a fluoride-releasing agent.

7. A one package, shelf-stable light-curing orthodontic band cement that comprises about 60 to about 75 weight percent finely divided inorganic filler, about 15 to about 30 weight percent of one or more dimethacrylate esters, zero to about twenty percent of one or more diluent mono- or trimethacrylate esters, to about 7 to about 15 weight percent of a dimethacrylate ester containing two carboxylic acid groups and a photo-curing system present in an amount sufficient to effect cure within about two minutes upon irradiation of said cement with light, wherein the weight ratio of the dimethacrylate ester portion plus diluent mono- or trimethacrylate ester portion to the two carboxylic acid-containing dimethacrylate ester portion is about 3:1 to about 1.5:1, and said methacrylates constitute about 25 to about 40 weight percent of said cement.

8. The light-curing band cement according to claim 7 wherein said finely divided inorganic filler is selected from the group consisting of silanized quartz, silica, fumed silica, zirconium, barium or strontium glass and silanized glass.

9. The light-curing band cement according to claim 7 wherein said dimethacrylate esters are selected from the group consisting of neopetylglycol dimethacrylate, decanediol-1,10-dimethacrylate, dodecanediol-1,12-dimethacrylate, 1,4-butanediol dimethacrylate, ethyleneglycol dimethacrylate, diethyleneglycol dimethacrylate, triethyleneglycol dimethacrylate, tetraethyleneglycol dimethacrylate, polyethyleneglycol dimethacrylate, propyleneglycol dimethacrylate, dipropyleneglycol dimethacrylate, tripropyleneglycol dimethacrylate, tetrapropyleneglycol dimethacrylate, polypropyleneglycol dimethacrylate, hexamethyleneglycol dimethacrylate, 2,2-bis(4-methacryloxy-phenyl)propane, 2,2-bis(4-methacryloxyethoxyphenyl)propane, 2,2-bis[4-(3-methacryloxy-2-hydroxypropoxy)phenyl]-propane, 1,2-bis(3-methacryloxy-2-hydroxypropoxy)ethane, 2,2-bis(4-methacryloxyphenyl)propane, 2-hydroxy-1,3-dimethacryloxypropane, di-2-methacryloxy-ethyl-2,2,4-trimethylhexamethylene dicarbamate, di-2-methacryloxyethylisophorone dicarbamate, and di-2-methacryoxyethyl-2,4- or 2,6-tolylene dicarbamate.

10. The light-curing orthodontic band cement according to claim 7 wherein one or more of said fillers or dimethacrylate esters includes a fluoride-releasing agent.

11. The light-curing band cement according to claim 7 packaged in an opaque container.

12. The light-curing band cement according to claim 1 packaged in an opaque container.

13. A process for affixing a dental band to a cleaned tooth that comprises the steps of:

(a) applying a light-curing orthodontic band cement according to claim 1 to an orthodontic band to be used, a tooth to be banded or both;

(b) placing the band of step (a) around the tooth of that step to form a banded tooth; and (c) irradiating the applied cement on the banded tooth with a cement-curing amount of light to form a tooth with a dental band affixed thereto.

14. A process for affixing a dental band to a cleaned tooth that comprises the steps of:

(a) applying a light-curing orthodontic band cement according to claim 7 to an orthodontic band to be used, a tooth to be banded or both;

(b) placing the band of step (a) around the tooth of that step to form a banded tooth; and (c) irradiating the applied cement on the banded tooth with a cement-curing amount of light to form a tooth with a dental band affixed thereto.

* * * * *